US012616424B2

(12) United States Patent
Son et al.

(10) Patent No.: US 12,616,424 B2
(45) Date of Patent: May 5, 2026

(54) ANATOMICAL MANIPULATION DEVICE

(71) Applicants: Matthew H. Son, Leonia, NJ (US);
Jung Hoon Son, New York, NY (US);
Chang-Oh Chu, Hwaseong-si (KR);
Hyeonbeom Chu, Seongnam-si (KR)

(72) Inventors: Matthew H. Son, Leonia, NJ (US);
Jung Hoon Son, New York, NY (US);
Chang-Oh Chu, Hwaseong-si (KR);
Hyeonbeom Chu, Seongnam-si (KR)

( * ) Notice: Subject to any disclaimer, the term of this
patent is extended or adjusted under 35
U.S.C. 154(b) by 0 days.

(21) Appl. No.: 19/055,432

(22) Filed: Feb. 17, 2025

(65) Prior Publication Data

US 2025/0345007 A1 Nov. 13, 2025

Related U.S. Application Data

(60) Provisional application No. 63/644,520, filed on May
9, 2024.

(51) Int. Cl.
*A61B 5/00* (2006.01)
*A61M 27/00* (2006.01)
(Continued)

(52) U.S. Cl.
CPC ......... *A61B 5/7292* (2013.01); *A61M 27/006*
(2013.01); *A61N 1/36031* (2017.08);
(Continued)

(58) Field of Classification Search
CPC ......... A61B 5/7292; A61B 2560/0219; A61M
27/006; A61N 1/36031; A61N 7/00;
G16H 20/00
See application file for complete search history.

(56) References Cited

U.S. PATENT DOCUMENTS 6,324,432 B1 * 11/2001 Rigaux .................. A61N 1/048
600/372
6,329,638 B1 * 12/2001 Bloodworth ........... A61H 23/02
601/18
(Continued)

FOREIGN PATENT DOCUMENTS

CN 112386473 A 2/2021

OTHER PUBLICATIONS

Soichi Ando et al., "Effects of electrical muscle stimulation on
cerebral blood flow," BMC Neuroscience, Nov. 14, 2021, pp. 1-7,
vol. 22, No. 67.

*Primary Examiner* — Mark W. Bockelman
(74) *Attorney, Agent, or Firm* — H&I PARTNERS; Chai
Im; C. Andrew Im

(57) ABSTRACT

An anatomical manipulation device having a plurality of
actuators configured around an anatomical interface. The
device includes a controller, an interactive communication
interface and at least one feedback sensor to measure physi-
ological responses. The interactive communication interface
receives input from the user. The controller coordinates the
operation of the actuators based on the measurements
received from the feedback sensor and input from the
interactive communication interface. Each actuator includes
one or more of: a high-intensity focused ultrasound (HIFU)
probe, an electrical muscle stimulator, a low-frequency
pulse generator, a sound wave generator and a micro-
vibrator.

17 Claims, 7 Drawing Sheets

(51) Int. Cl.
  *A61N 1/36*          (2006.01)
  *A61N 7/00*          (2006.01)
  *G16H 20/00*        (2018.01)

(52) U.S. Cl.
  CPC .............. *A61N 7/00* (2013.01); *G16H 20/00*
          (2018.01); *A61B 2560/0219* (2013.01)

(56)                  References Cited

U.S. PATENT DOCUMENTS

| 6,449,509 | B1 * | 9/2002 | Park ................... A61N 1/36521 |
| | | | 600/533 |
| 6,942,686 | B1 * | 9/2005 | Barbut ..................... A61F 7/12 |
| | | | 607/105 |
| 10,456,573 | B1 * | 10/2019 | Feinstein ............... A61B 5/026 |
| 2006/0111659 | A1 * | 5/2006 | Tyler ................... A61B 5/6864 |
| | | | 604/9 |
| 2010/0198322 | A1 * | 8/2010 | Joseph ................... A61F 7/007 |
| | | | 607/108 |
| 2015/0202427 | A1 | 7/2015 | Tucker et al. |
| 2019/0262212 | A1 * | 8/2019 | Schroeder ............ A61H 1/0296 |
| 2019/0374428 | A1 * | 12/2019 | Kaufman ........... A61N 1/39044 |
| 2020/0147382 | A1 | 5/2020 | Caban et al. |
| 2022/0016444 | A1 * | 1/2022 | Park ........................ A61N 7/00 |
| 2022/0072128 | A1 * | 3/2022 | Airan ...................... A61N 7/00 |
| 2022/0409080 | A1 * | 12/2022 | Kyriacou ............... A61B 5/031 |
| 2023/0092566 | A1 * | 3/2023 | Kamler ................. G01N 29/34 |
| | | | 600/301 |
| 2023/0181934 | A1 * | 6/2023 | Park .................... H10N 30/852 |
| | | | 601/2 |
| 2024/0050744 | A1 | 2/2024 | Ludwig et al. |
| 2024/0198063 | A1 * | 6/2024 | Golanov ........... A61N 1/36135 |

* cited by examiner

1400

1300

1600

ANATOMICAL MANIPULATION DEVICE

RELATED APPLICATION

This application claims the benefit of U.S. Provisional Application No. 63/644,520 filed May 9, 2024, which is incorporated herein by reference in its entirety.

FIELD OF THE INVENTION

The claimed invention relates generally to anatomical manipulation device, more specifically, to a programmable device for application of focused manipulation techniques around scalp, head and neck regions of a user.

BACKGROUND OF THE INVENTION

The growth of the 65 and over US population from 2020 to 2023 is striking: up 9.4% to approximately 59.2 million nationally. There are currently roughly 62 million adults ages 65 and older living in the U.S., accounting for 18% of the population. By 2054, it is estimated that 84 million adults ages 65 and older will make up 23% of the population.

As the elderly population increases rapidly, various diseases related to this demographic are emerging as significant socioeconomic issues. Among these, age-related cognitive decline is very common and has multiple contributing factors. Around 40% of dementia risk is attributable to modifiable risk factors such as physical inactivity, hypertension, diabetes and obesity.

Recently, sleep disorders, including obstructive sleep apnea (OSA), have been considered among these factors. OSA is common, particularly after the age of 65 years, when it has an estimated prevalence of at least 20%. Insufficient or poor-quality sleep affects the immune system, weight management, glucose metabolism, cardiovascular and cerebrovascular health, cognition, work productivity, psychological well-being, and public safety. Obstructive sleep apnea (OSA) leads to intermittent hypoxemia and changes in sleep macro- and microarchitecture. Intermittent hypoxemia probably causes systemic and brain responses that include metabolic disturbances/diabetes, oxidative stress, inflammation, hypertension, blood-brain barrier dysfunctions, and brain edema. These responses, combined with the altered sleep macro- and micro-architecture, may lead to small-vessel disease, microinfarcts, strokes, reduced neurogenesis, reduced synaptic plasticity, decreased cognitive functioning, changes in brain white and gray matter, changes in cerebral networks, and abnormal levels of Alzheimer's disease (AD) biomarkers, which can all be involved in abnormal cognitive decline and dementia.

Recent findings also indicate that sleep participates in the production and clearance of brain metabolic products including those involved in dementia pathogenesis. AD is an age-dependent disease marked by the accumulation of specific proteins, neurofibrillary tangles, and amyloid B peptide, in the brain. These proteins are proposed to be cleared by the waste clearance system, thus reduced movement of cerebrospinal fluid (CSF) from the periarterial spaces to the brain parenchyma via aquaporin-4 (AQP4) could facilitate protein accumulation in the brain. Research on brain fluids also indicates that OSA might impair the CSF's flow, reducing the brain's ability to maintain homeostasis and exacerbate neurovascular issues, further affecting sleep quality and health outcomes. Neurons help flush waste out of brain during sleep.

Reversely, recent research highlights the role of CSF dynamics in sleep disorders, particularly obstructive sleep apnea (OSA). The CSF and glymphatic systems, which manage fluid and waste clearance in the brain, are closely linked to sleep quality. During sleep, especially deep sleep, cerebrospinal fluid helps flush out toxins like amyloid B. Cerebrospinal fluid surrounding the brain enters and weaves through intricate cellular webs, collecting toxic waste as it travels. Upon exiting the brain, contaminated fluid must pass through a barrier before spilling into the lymphatic vessels in the dura mater—the outer tissue layer enveloping the brain underneath the skull. The production of cerebrospinal fluid by the choroid plexuses is believed to be relatively constant; however, the cerebrospinal fluid secretion varies over the duration of a day with an average production of 650 ml and maximal production after midnight. By enhancing CSF dynamics—whether through physical therapy targeting the cervical spine, improving venous return, or addressing issues like intracranial pressure—there could be a reduction in brainstem compression. This would likely aid in reducing apnea episodes during sleep and improving overall respiratory patterns during rest.

One of the essential functions of the CSF system is the maintenance of central nervous system (CNS) homeostasis. As the central nervous system consists of highly active metabolic regions, waste products need to be cleared. The most recently proposed mechanism for waste clearance is the highly debated glymphatic system. The glymphatic system is a fluid conduit defined as an astrocyte-mediated fluid exchange of CSF and insulin sensitivity factor (ISF) in the brain. Within the glymphatic system, CSF is thought to be driven from the subarachnoid space into the periarterial spaces surrounding penetrating arteries. The meningeal lymphatic vessels are embedded within the dura mater alongside arteries, veins, and cranial nerves. Here they create a network that facilitates waste clearance away from the brain and a direct link between the central nervous system and the peripheral immune system. The spinal cord has a waste clearance system and a lymphatic system resembling the systems proposed for the brain. In addition, the CSF system constitutes a crucial role in the CNS as it provides mechanical protection, ensures homeostasis, and facilitates communication between the CNS and peripheral nervous system, lymphatic system, vascular system, and immune system. Studying the brains of sleeping mice, the researchers found that neurons drive cleaning efforts by firing electrical signals in a coordinated fashion to generate rhythmic waves in the brain. Individual nerve cells coordinate to produce rhythmic waves that propel fluid through dense brain tissue, washing the tissue in the process. Without these waves, fresh cerebrospinal fluid could not flow through the silenced brain regions and trapped waste couldn't leave the brain tissue. That's how sleep cleanses the brain. Enhancing CSF dynamics may be generating the rhythmic waves in the brain.

Impaired cerebrospinal fluid circulation may affect the removal of metabolic waste during sleep, contributing to the development or worsening of sleep disorders. Any alteration in the cerebrospinal fluid system may be influenced by other factors, e.g., aging, hypertension, atherosclerosis, and sleep deprivation and may influence other parts of the cerebrospinal fluid system. An obstruction of normal cerebrospinal fluid flow is the main reason of hydrocephalus which makes it a serious and life-threatening neurological disorder. Improving cerebrospinal fluid dynamics is also important for managing conditions related to elevated intracranial pressure, such as idiopathic intracranial hypertension (IIH), hydrocephalus, or even chronic headaches. Enhancing cerebrospinal fluid flow and pressure regulation can also indirectly benefit conditions like obstructive sleep apnea (OSA) by generating rhythmic waves in the brain and reducing venous pressure and relieving brainstem compression.

Among several ways cerebrospinal fluid dynamics can be improved, physical therapies focused on gentle movements can help improve venous drainage, particularly for the head and neck. This can help reduce cerebrospinal fluid pressure by improving venous return from the brain. For example, exercises that target the cervical spine and focus on maintaining a neutral head position have been shown to improve venous outflow by preventing compression of key vessels like the internal jugular veins. The soft tissue mobilization of the device also relaxes the upper trapezius, sternocleidomastoid (SCM), and scalene muscles, which can become tense and contribute to venous obstruction in the neck. Research on soft tissue mobilization, particularly for the upper trapezius, sternocleidomastoid (SCM), and scalene muscles, suggests that these therapies can be highly beneficial for reducing tension and addressing venous obstruction in the neck region. These muscles often become tight or strained due to poor posture, repetitive movements, or mechanical neck pain, leading to various symptoms, including venous and lymphatic drainage issues.

Studies show that in patients with mechanical neck pain or thoracic outlet syndrome, releasing tension in these muscles can alleviate pressure on blood vessels and nerves, improving venous return and reducing symptoms like headaches, shoulder pain, and even upper extremity numbness. CranioSacral Therapy (CST) or manipulation of the cervical spine (MCS) is another manual therapy to improve cerebrospinal fluid dynamics. A gentle, hands-on technique used to promote the flow of cerebrospinal by addressing tension patterns in the skull, spine, and sacrum. It's thought to encourage better movement of cerebrospinal fluid by freeing up restrictions in the cranial bones and dura mater (the outer layer of the brain and spinal cord). CST involves very light pressure (5 g), typically applied to areas like the head and neck, and focuses on encouraging the body's self-healing mechanisms by improving the movement of cerebrospinal fluid. Craniosacral therapy (manipulation of the cervical spine: MCS), which involves gentle pressure on the head and neck, has been explored as a treatment for post-traumatic stress disorder (PTSD) and dementia. Joint mobilizations also improve mobility in the cervical and upper thoracic spine. Restricted motion in the cervical vertebrae (especially C1 and C2) can affect venous outflow from the brain.

The Atlanto-occipital mobilization around the base of the skull (the occiput) and the top cervical vertebra (C1) the claimed device provides can relieve pressure on the vertebral and jugular veins, enhancing blood and cerebrospinal fluid flow. Atlanto-occipital mobilization is a manual therapy technique focused on the junction between the base of the skull (the occiput) and the first cervical vertebra (C1, also known as the atlas). This area is critical for both neurological and vascular function due to its proximity to the brainstem, vertebral arteries, jugular veins, and cerebrospinal fluid pathways. Mobilizing the Atlanto-occipital joint can help reduce tension and restrictions in the surrounding soft tissues, such as muscles and fascia. Tension in this region can restrict normal blood and cerebrospinal fluid flow. For example, tight muscles like the suboccipital muscles or the trapezius can compress vessels or impinge on structures involved in cerebrospinal dynamics. Mobilization releases this tension, potentially allowing cerebrospinal fluid to flow more freely between the brain and spinal cord. The jugular veins and vertebral veins run through the cervical region, and when they are compressed due to poor posture or muscle tightness, venous blood return from the brain can be impaired. This restriction can indirectly affect cerebrospinal fluid dynamics, as proper venous drainage is necessary for balanced cerebrospinal fluid production and reabsorption. Atlanto-occipital mobilization may help relieve pressure on these veins, improving venous outflow and thus helping balance intracranial pressure and cerebrospinal fluid circulation. Cerebrospinal fluid circulates in the subarachnoid space, which extends from the brain to the spinal cord. Restrictions or misalignments at the Atlanto-occipital joint can impair the movement of cerebrospinal fluid between the cranium and the spinal cord. By mobilizing this joint, the claimed device aims to free up restrictions, promoting smoother cerebrospinal flow across the craniospinal axis. This is particularly important for conditions where cerebrospinal fluid pressure is elevated, such as in idiopathic intracranial hypertension or after trauma. The dura mater, a thick membrane surrounding the brain and spinal cord, attaches at key points along the spine, including the upper cervical area. Tension or restrictions in the dura mater can disrupt cerebrospinal fluid flow.

SUMMARY AND OBJECT OF THE INVENTION

The claimed device employs pre-programmed evidence-based manipulation protocols suited to address underlying mechanisms of various medical conditions as a default. Additionally, feedback sensors like ultrasound blood flow quantification, EEG brain activity monitoring among others provide real-time physiology data to an AI optimization engine. The AI algorithm continuously interprets the feedback data to provide actionable alerts. This enables therapy adaptation to augment circulation, pressure or waste drainage to better the default modes and tailor to individual user needs via data-driven enhancement in an intelligent secondary manipulation mode. Feedback data can help individuals learn to relax more effectively, by showing real-time changes in their physiological responses.

Heart Rate Variability (HRV) feedback tracks the intervals between heartbeats. Improving HRV through relaxation techniques can help reduce stress and enhance autonomic function. Electromyography (EMG) electrode measures muscle activity, helping individuals identify tension in specific muscle groups and work towards relaxation, particularly useful in pain management or rehabilitation. Electroencephalography (EEG) feedback, or neurofeedback, monitors brain wave activity. It's used in the treatment of conditions like ADHD, anxiety, and PTSD by training the brain to adopt healthier patterns. Thermal feedback tracks skin temperature, which can decrease during stress. Training with this data helps individuals learn to improve blood flow and relaxation responses. Galvanic Skin Response (GSR) measures changes in sweat gland activity, often linked to emotional arousal or stress. It is commonly used in stress management and emotional regulation training.

Heart Rate Variability (HRV) and Electroencephalography (EEG) feedback are used to help individuals manage conditions like insomnia by promoting relaxation and improving sleep patterns. Neurofeedback (EEG) is also used to alter abnormal brain wave patterns linked to anxiety and trauma, helping patients achieve a more balanced mental state. One study demonstrated that ultrasound was effective at monitoring the flow within the ventriculoperitoneal shunt systems and detected cranial-to-peritoneal flow in patients with such implants. It also identified differences in peak velocities between proximal and distal catheter sections, highlighting the utility of ultrasound for assessing cerebrospinal fluid dynamics in the neck region. This could have implications for monitoring other neck-based CSF flow conditions.

Its carotid ultrasound probes are a safe, noninvasive, painless procedure that uses sound waves to examine the blood flow through the carotid arteries. The 4-MHz ultrasound probes on each side of the neck achieve a depth of −78 mm targeting carotid arteries. In accordance with an exemplary embodiment of the claimed invention, FIG. 1 shows a Carotid High Intensity Focused Ultrasound (HIFU) probe in the middle with electrical muscle stimulators (EMS).

These arteries deliver blood from the heart to the brain. A carotid ultrasound tests for blocked or narrowed carotid arteries, which can increase the risk of stroke. The results of the test can help your health care provider determine a treatment to lower your stroke risk. High Intensity Focused Ultrasound (HIFU) operates by focusing ultrasound waves onto a targeted area like deep cervical lymph nodes of neck, generating heat and mechanical forces that can affect tissues. There are an estimated 300 lymph nodes in the neck. Among the estimated 300 cervical lymph nodes in the neck, HIFU probes address deep cervical lymph nodes including lateral jugular, anterior jugular, and jugulodigastric nodes.

The claimed system therefore grounds overall treatment in proven therapeutic technique baselines matching specific conditions, with the flexibility to biologically tune delivery beyond standardized protocols to optimize efficacy over the course of care via sensor-informed optimization routines.

For example, while increased perfusion is beneficial for recovery in certain injuries, excessive intracranial pressure can be detrimental. And where Alzheimer's patients require maximizing waste drainage flows, those with hypotension warrant cautious blood flow changes. An intelligent, evidence-based manipulation treatment system is needed.

In accordance with an exemplary embodiment of the claimed invention, an anatomical manipulation device comprises a plurality of actuators configured around an anatomical interface. The device includes a controller, an interactive communication interface and at least one feedback sensor to measure physiological responses. The interactive communication interface receives input from the user. The controller coordinates the operation of the actuators based on the measurements received from the feedback sensor and input from the interactive communication interface.

In accordance with an exemplary embodiment of the claimed invention each actuator comprises one or more of: high-intensity focused ultrasound (HIFU) probe, an electrical muscle stimulator, a low-frequency pulse generator, a sound wave generator, and a micro-vibrator. The HIFU probe performs at least one of the following: target deep cervical lymph nodes, monitor blood flow at configurable intervals and store measured flow response data. The electrical muscle stimulator provides targeted muscle activation, adjusts intensity based on the measurements from the feedback sensor, synchronizes with other therapeutic stimulators and prevents muscle fatigue through adaptive timing. The low-frequency pulse generator operates in a pulse frequency range of 1-50 Hz for relaxation, recovery, muscle strength and endurance training. The sound wave generator examines blood flow through carotid arteries of the user. The micro-vibrator is positioned to target anatomical areas affecting cranial, cervical, and upper back fluid drainage and circulation. Preferably, the plurality of actuators is arranged in a pattern around the anatomical interface to enable a sequential activation from posterior to anterior positions In accordance with an exemplary embodiment of the claimed invention, the aforesaid controller coordinates activation sequences of the actuators, modifies therapeutic parameters based on the measurements from the feedback sensor, stores effective activation patterns for future use, and modifies a timing between activation of the actuators.

In accordance with an exemplary embodiment of the claimed invention, the aforesaid interactive communication interface provides a real-time visualization of a therapeutic activity, a spatial tracking to monitor a therapeutic output and a gesture control to enable a user to adjust therapeutic parameters. Preferably, the interactive communication interface provides a real-time 2D or 3D visualization of the therapeutic activity.

In accordance with an exemplary embodiment of the claimed invention, the aforesaid feedback sensor comprises one of the following: an electromyographic (EMG) electrode, an electroencephalography (EEG) sensor to monitor brain activity, a heart rate sensor and a Doppler sensor to monitor and diagnose ultrasound blood flow quantification.

In accordance with an exemplary embodiment of the claimed invention, the aforesaid controller analyzes deviations from baseline measurements and coordinates activation of a set of the actuators in one of the stored effective patterns.

In accordance with an exemplary embodiment of the claimed invention, the aforesaid Doppler sensor comprises a HIFU probe to generate ultrasound waves within a frequency range of 4.4-7.7 MHz and electrical muscle stimulators on each side of the ultrasound probe. The electrical muscle stimulators provide percussive pulsations.

In accordance with an exemplary embodiment of the claimed invention, the aforesaid ultrasound probe comprises a thermal pad to stimulate a flow of blood and cerebrospinal fluid along a lymphatic vessel and a lymph node to prevent accumulation of beta amyloid and tau proteins in user's brain and body. A piezoelectric transducer is enclosed within the thermal pad. The piezoelectric transducer reduces noise coupling, enhances resolution and enables gel-free acoustic coupling. The piezoelectric transducer transmits bounced-back feedback waves to the controller.

In accordance with an exemplary embodiment of the claimed invention, the aforesaid micro-vibrator targets the Atlanto-occipital joint, automatically adjusts based on the measurements, and coordinates timing with HIFU therapy. For a therapeutic purpose, the micro-vibrator maintains vibration within a frequency range of 0.75-7.5 MHz.

In accordance with an exemplary embodiment of the claimed invention, the aforesaid micro-vibrator is configured to improve venous drainage from a user's head and neck and configured to reduce a cerebrospinal fluid pressure by improving venous return from the user's brain.

In accordance with an exemplary embodiment of the claimed invention, the soft tissue mobilization of the micro-vibrator relaxes upper trapezius, sternocleidomastoid (SCM), and scalene muscles, thereby reducing a venous obstruction in the user's neck.

In accordance with an exemplary embodiment of the claimed invention, the aforesaid controller coordinates the operation of the actuators by one of the following: sequentially activating the actuators one at a time, in a synchronized intensity modulation, or in a wave activation sequence. Each step in the wave activation sequence can have different pitch, duration, fine tuning, level, and cross-fade amount.

In accordance with an exemplary embodiment of the claimed invention, based on the measurements from the feedback sensor, the aforesaid controller triggers at least one of the following: predefined actuator combination responses, adaptive pattern modifications, intensity adjustments across multiple actuators and modification to activation timing and sequence of the actuators.

In accordance with an exemplary embodiment of the claimed invention, the aforesaid actuators are activated in one of the following programmed patterns: a drainage enhancement sequence, a circulation improvement combination, a pressure relief pattern, and a tissue mobilization sequence.

In accordance with an exemplary embodiment of the claimed invention, the aforesaid controller analyzes therapy effectiveness through at least one of the following: comparison of pre-measurements and post-measurements, trend analysis across sessions, identification of optimal therapeutic parameters and patient-specific response patterns.

In accordance with an exemplary embodiment of the claimed invention, the aforesaid controller further comprises preset manipulation protocols optimized for a predetermined medical condition and adaptive lesson plans to customize therapy based on user feedback.

In accordance with an exemplary embodiment of the claimed invention, the aforesaid anatomical manipulation device further comprises at least one of the following feedback devices: a wearable device, a smartphone, a tablet, a laptop, a personal computer, a virtual reality/augmented reality (VR/AR) headset.

In accordance with an exemplary embodiment of the claimed invention, the aforesaid anatomical manipulation device further comprises a power supply. The controller manages power of the power supply by at least one of the following: adjusting monitoring frequency based on power availability, prioritizing therapeutic functions over data collection, optimizing sampling rates for battery life, and enabling enhanced monitoring when an external power source is utilized.

In accordance with an exemplary embodiment of the claimed invention, the aforesaid power supply is a rechargeable battery or an external power source.

In accordance with an exemplary embodiment of the claimed invention, an adaptable head and neck manipulation device comprises a core massager configured to target therapeutic drainage and circulation improvement in the cranial, cervical and upper back regions. The massager employs various massage and manipulation techniques focused on areas including Atlanto-occipital joint, suboccipital muscles and lymph nodes to enhance cerebrospinal, glymphatic, lymphatic, interstitial fluid and blood drainage patterns. Studies have shown that massage can enhance endothelial function (the lining of blood vessels), promoting vascular relaxation and improved circulation.

In accordance with an exemplary embodiment of the claimed invention, the system comprises actuated components capable of performing techniques grounded in established clinical methodologies and recent research. It allows for variable force application, pattern customization, and technique adaptation based on the feedback data.

Interchangeable attachments and software expand the core functionality to accommodate different manipulation methods and analytics. Baseline protocols matched to medical conditions provide initial manipulation parameter guidance with custom tuning enabled by modular sensor integration.

In accordance with an exemplary embodiment of the claimed invention, the aforesaid anatomical manipulation device enables therapy adaptation to augment circulation, pressure or waste drainage to better the default modes and tailor to individual user needs via data-driven enhancement in an intelligent secondary manipulation mode. Additionally, the aforesaid device uses High Intensity Focused Ultrasound for monitoring and therapeutic purposes at the same time. Equipped with micro-vibrating elements targeting Atlanto-occipital joint, suboccipital muscles and lymph nodes to enhance cerebrospinal, glymphatic, lymphatic, interstitial fluid and blood drainage patterns. Altogether, the claimed device relaxes tension of muscles and veins, aiding deep sleep and enhancing CSF dynamics.

Overall, an adaptable anatomical manipulation platform centered on a functional cranial and cervical massage core, with capabilities to have its therapeutic approach augmented through supplemental software and hardware modules. The goal is improved fluid drainage and circulation via integrated, customized manipulation protocols targeting key head and neck regions.

BRIEF DESCRIPTION OF FIGURES

The following detailed descriptions, given by way of example, and not intended to limit the present invention solely thereto, will be best be understood in conjunction with the accompanying figures.

DETAILED DESCRIPTION OF THE EMBODIMENTS

Core Sensor Components

As exemplary shown in FIGS. 1-4, the anatomical manipulation device 1000 comprises at least three actuators 1100 connected thereon via the actuator connectors 1200. Each actuator connector 1200 electrically and removably connects the actuator 1100 to the anatomical manipulation device 1000. In accordance with an exemplary embodiment of the claimed invention, each actuator 1100 comprises one type of therapeutic stimulators among high-intensity focused ultrasound (HIFU) probes 1400, electrical muscle stimulators (EMS) 1500, a low-frequency pulse generator, a sound wave generator and micro-vibrators 3000.

Figure 1:
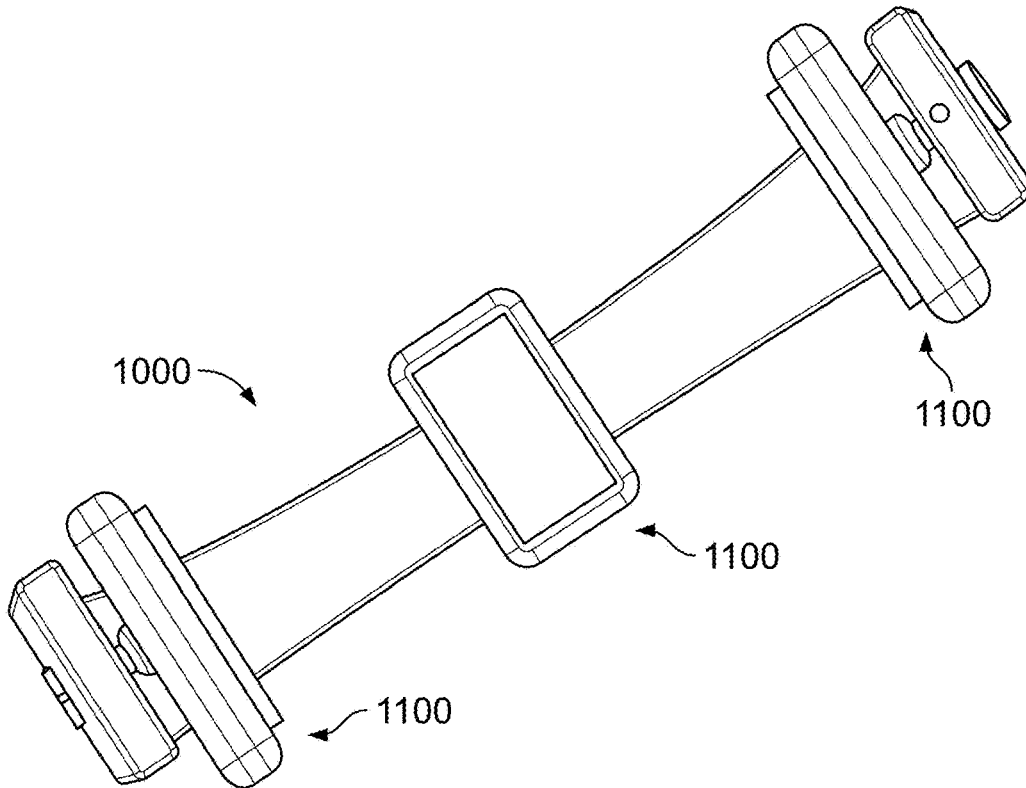
FIG. 1 is a perspective view of an anatomical manipulation device to stimulate cerebral blood flow and cerebrospinal fluid in accordance with an exemplary embodiment of the claimed invention.
Figure 2:
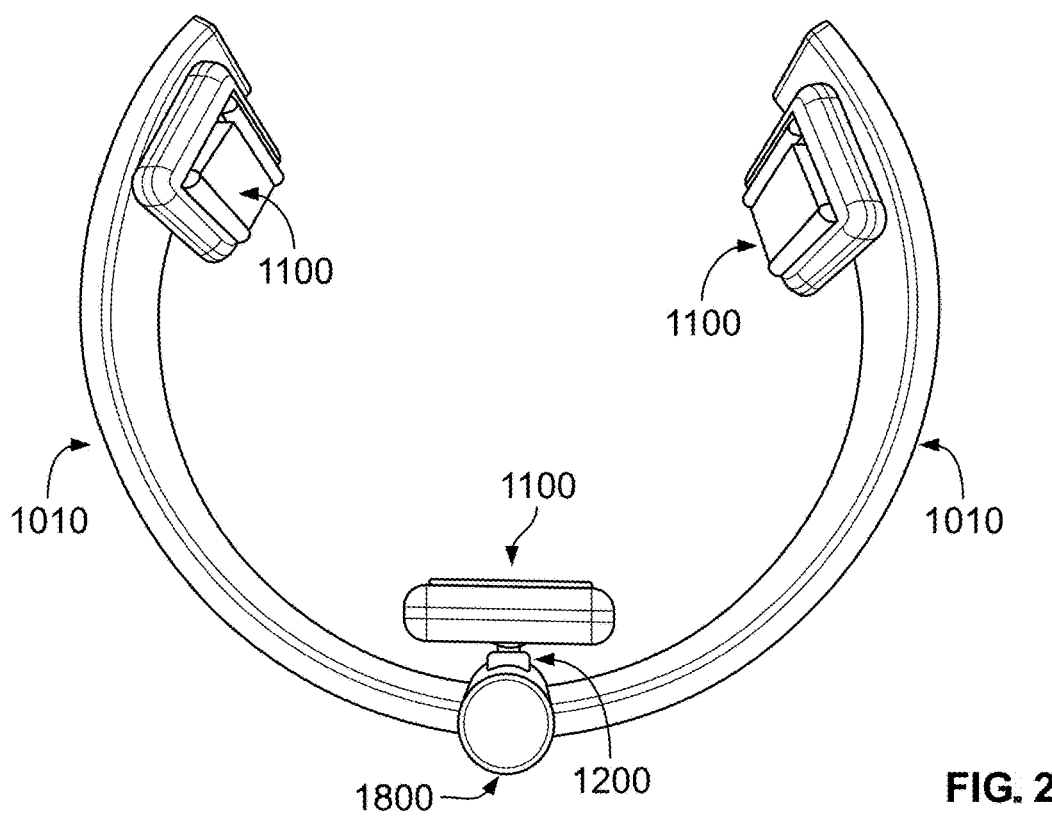
FIG. 2 is a perspective view of the anatomical manipulation device with the actuators connected to the actuator connectors in accordance with an exemplary embodiment of the claimed invention.
Figure 3:
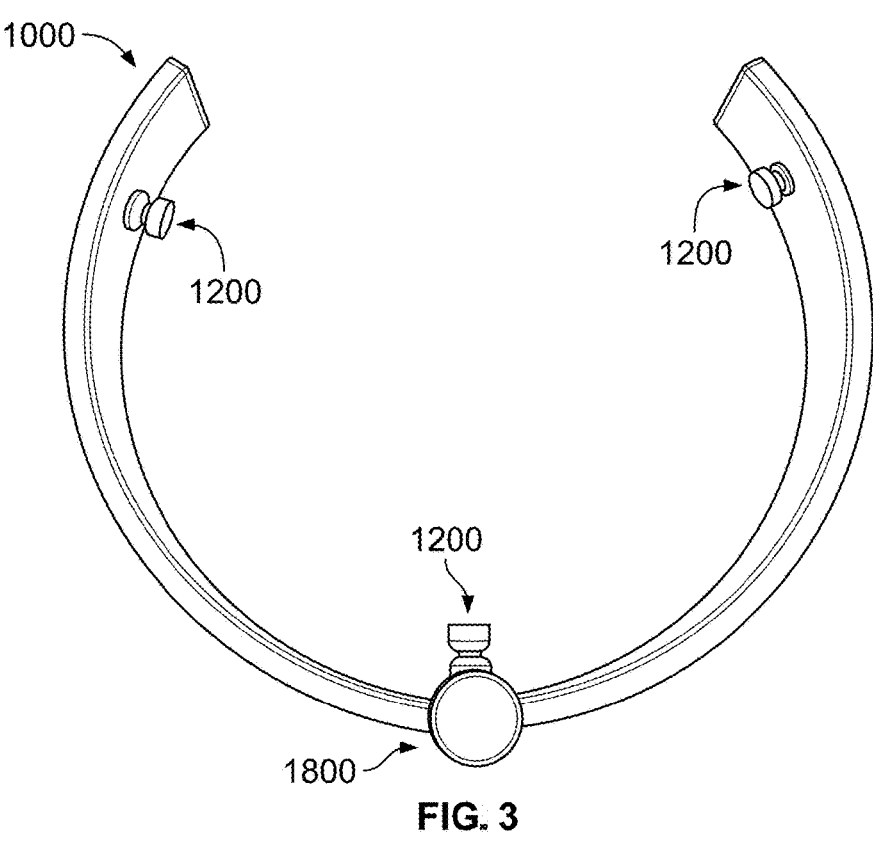
FIG. 3 is a perspective view of the anatomical manipulation device without the actuators connected to the actuator connectors in accordance with an exemplary embodiment of the claimed invention.
Figure 4:
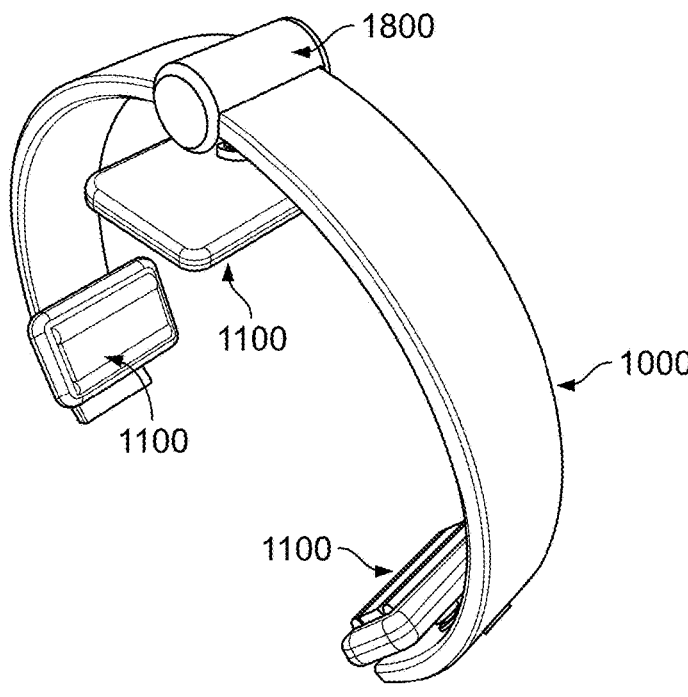
FIG. 4 is a perspective view of the anatomical manipulation device with the actuators in accordance with an exemplary embodiment of the claimed invention.
Figure 5:
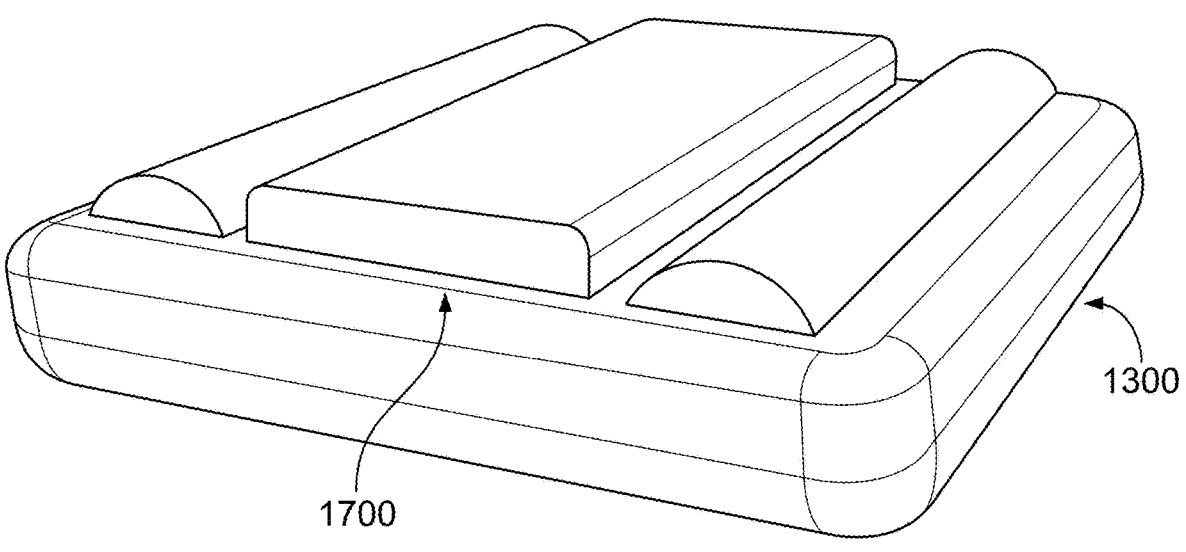
FIG. 5-9 show the actuators with different therapeutic stimulators in accordance with an exemplary embodiment of the claimed invention.
Figure 6:
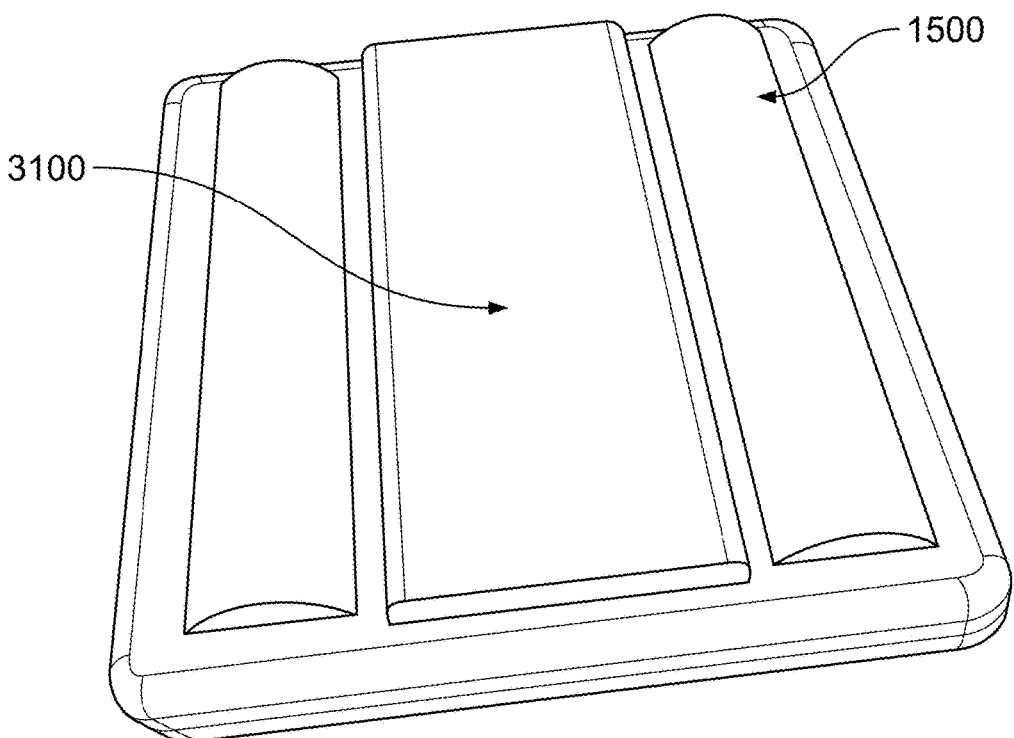
Figure 7:
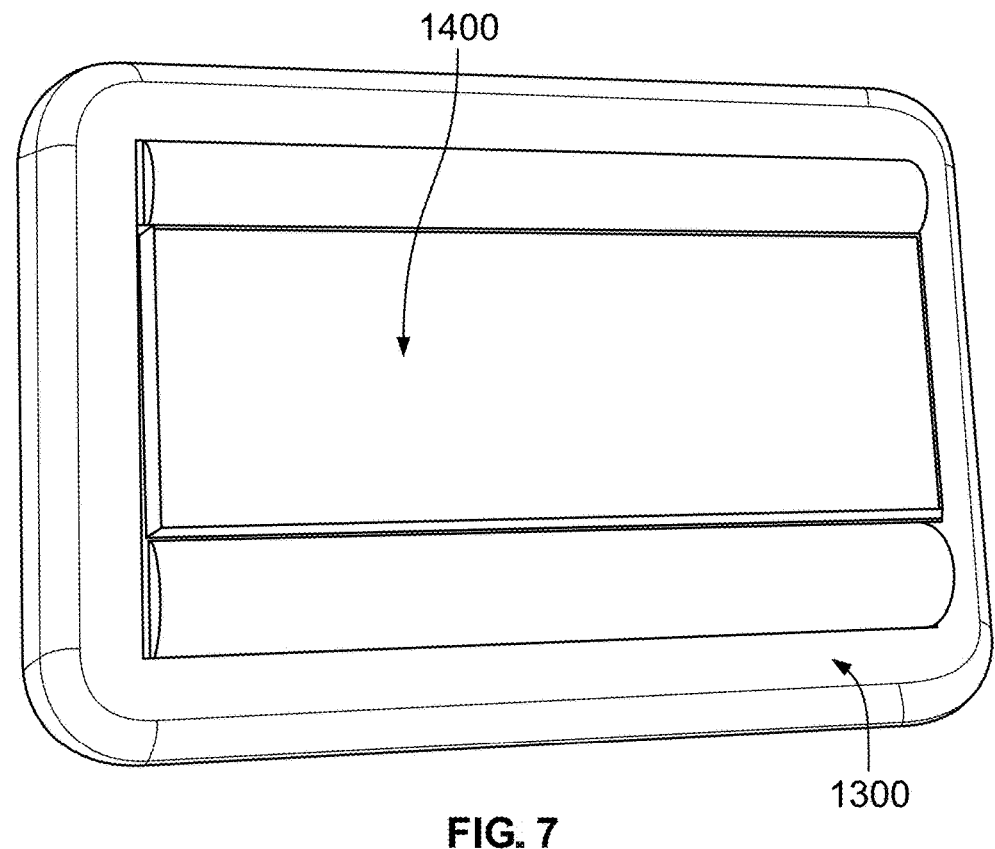

In accordance with an exemplary embodiment of the claimed invention, at least one actuator 1000 comprises a Doppler sensor 1300. The Doppler sensor 1300 monitor ultrasound blood flow quantification and EEG brain activity. The Doppler sensor 1300 monitors and diagnoses processes beneath the skin or even deep within the body, such as blood pressure as well. In accordance with an exemplary embodiment of the claimed invention, as shown in FIGS. 5 and 7, each Doppler sensor 1300 comprises either a piezoelectric transducer 1700 or an ultrasound probe 1400. Preferably, the piezoelectric transducer 1700 or the ultrasound probe 1400 is in the middle with electrical muscle stimulators 1500 on both sides of either the ultrasound probe 1400 or the piezoelectric transducer 1700.

Figure 8:
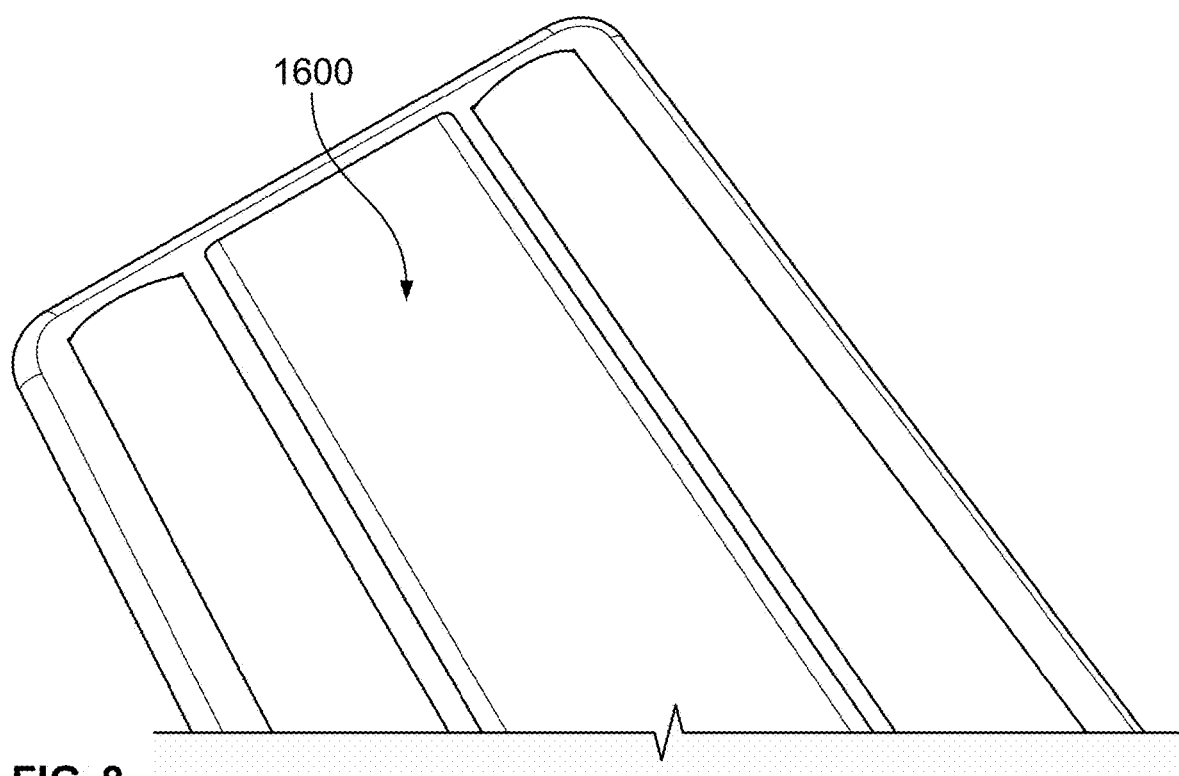

In accordance with an exemplary embodiment of the claimed invention, as shown in FIG. 8, the piezoelectric transducer 1700, a feedback sensor, is enclosed within a thermal pad 1600. The piezoelectric transducer 1700 reduces noise coupling, enhances resolution, enables gel-free acoustic coupling and ensures probe durability. The piezoelectric transducer 1700 targets major arteries, for example, carotid and femoral arteries. The piezoelectric transducer 1700 reads and delivers bounced-back feedback waves to the controller 2000 to analyze the feedback data.

Controller

Figure 12:
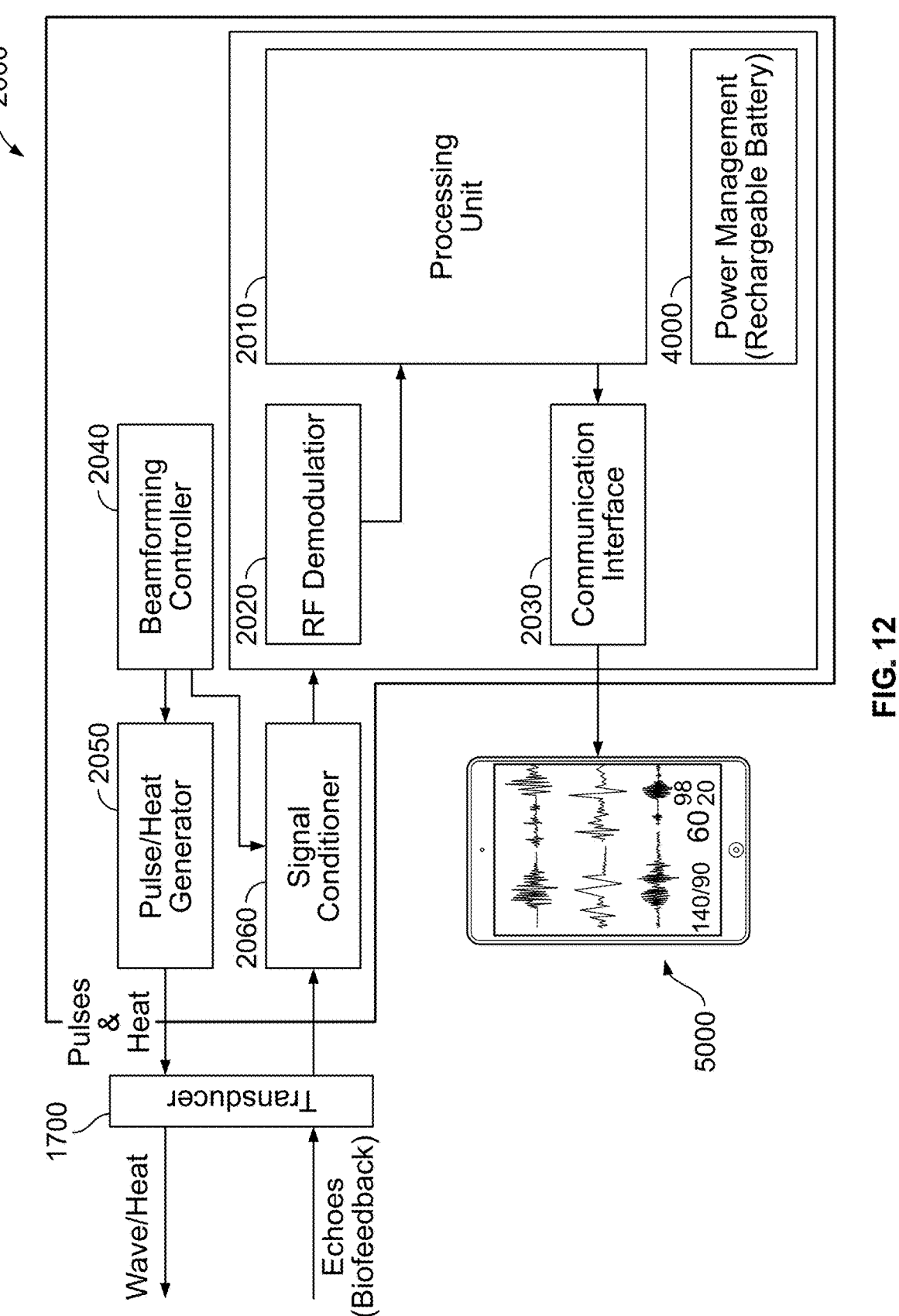
FIG. 12 is a schematic diagram of the controller in accordance with an exemplary embodiment of the claimed invention.

In accordance with an exemplary embodiment of the claimed invention, as shown in FIG. 12, the controller 2000 is a microcontroller, digital signal controller, a digital signal processor or the like. Controller 2000 comprises a processing unit 2010, e.g., a microcontroller/processor, radiofrequency (RF) demodulator 2020, a communication interface 2030, a power management module 4000, e.g., rechargeable battery, beamforming controller 2040, pulse/heat generator 2050 and signal conditioner 2060.

In accordance with an exemplary embodiment of the claimed invention, the controller 2000 manages how the actuators 1100 operate, process data, and communicates with external systems. The beamforming controller 2040 and the pulse/heat generator 2050 generate electrical signals of high-frequency pulses and the signals are sent to the actuators 1100, e.g., the piezoelectric transducer 1700 which converts the electrical pulses into ultrasound waves. The piezoelectric transducer 1700 emits the waves into target areas being measured and receives the echoes, bounced back from the target area. The echoes received by the piezoelectric transducer 1700 are processed by the signal conditioner 2060 with input from the beamforming control 2040 and the RF demodulator 2020 so that this data can be processed by the processing unit 2010. The processing unit 2010 collects the data from the feedback sensor, e.g., the piezoelectric transducer 1700 or Doppler sensor 1300 or EMG electrode 3100 or ultrasound probes 1400 and analyzes the time delay between sending the pulse and receiving the echo. The controller 2000 accurately manages the timing of both the emission and reception of ultrasound pulses. Controller 2000 determines the duration for which ultrasound pulses are emitted and sets the waiting period for receiving the echo from the target surface.

Using the time-of-flight data, controller 2000 calculates the distance between the Doppler sensor 1300 and the object. The speed of sound in the medium is typically known (e.g., about 343 m/s in air at room temperature), so the distance is calculated using the equation:

$$Distance = \frac{Time\ of\ Flight \times Speed\ of\ Sound}{2}$$

The controller 2000 filters out noise or irrelevant data from the received signal to improve accuracy. For example, weak echoes or reflections from distant objects may be ignored if they fall below a certain threshold.

After processing the signal and calculating the distance, the controller 2000 outputs the data in digital format for processing to an external device 5000, such as a tablet, laptop and the like, via the communication interface 2030. The controller 2000 also implements logic to ensure continuous operation such as managing the transmit and receive cycle for periodic measurements, handling interrupts or events when certain thresholds are met and performing temperature compensation if needed, since the speed of sound waves varies with temperature.

Core Manipulation Components

Figure 9:
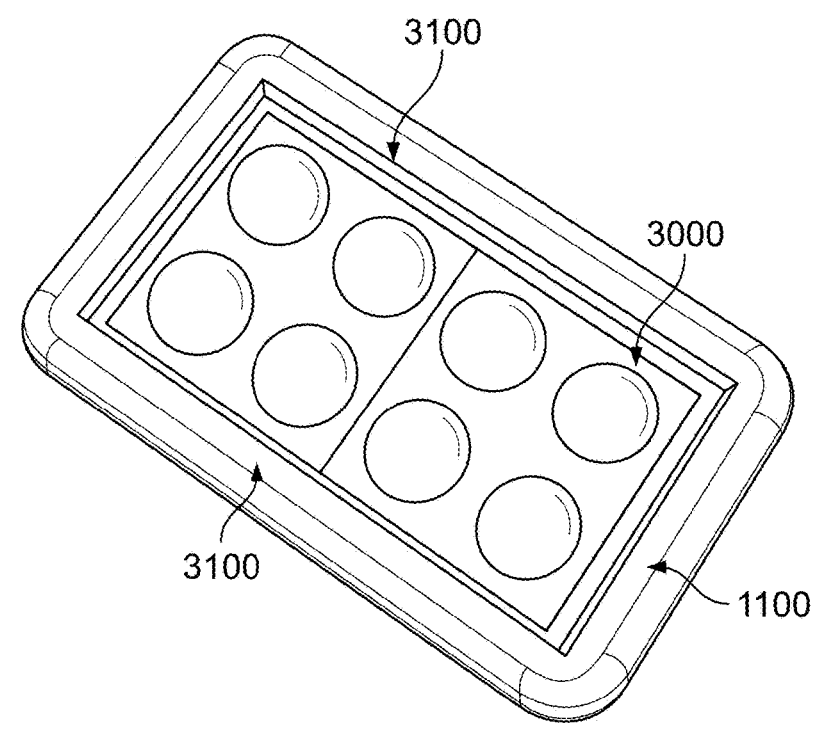

In accordance with an exemplary embodiment of the claimed invention, as shown in FIG. 9, the actuator 1100 comprises internally housed high-intensity focused ultrasound (HIFU) micro vibrating massagers or micro-vibrators 3000 strategically positioned to target key anatomical areas affecting cranial, cervical, and upper back fluid drainage and circulation. In order to improve venous drainage, particularly from the head and neck, the micro-vibrators 3000 can help reduce cerebrospinal fluid pressure by improving venous return from the brain. Preferably, as exemplary shown in FIG. 9, the actuator 1100 comprising the micro-vibrators 3000 additionally comprise EMG electrodes 3100, a feedback sensor.

The soft tissue mobilization of micro-vibrators 3000 also relaxes the upper trapezius, sternocleidomastoid (SCM), and scalene muscles, which can become tense and contribute to venous obstruction in the neck.

In accordance with an exemplary embodiment of the claimed invention, the ultrasound probes 1400 supports multiple probe frequencies: 2.5, 3.0, 3.5, 4.0, 5.0 MHz. The ultrasound probes 1400 can continuously monitor and diagnose processes under the skin or even deep within the body, such as blood pressure.

In accordance with an exemplary embodiment of the claimed invention, the ultrasound probes 1400 allows for continuous tracking of physiological signals from tissues as deep as 164 mm. The ultrasound waves also generate mechanical vibration at much higher frequencies, which allows them to penetrate deeper into major arteries. The ultrasound waves cause tissue particles to oscillate, generating heat and increasing cellular activity, making it highly effective for deep-tissue treatment. The heat increases blood flow, relaxes stiffness, and promotes the healing process by improving the oxygen and nutrient supply to the affected area. The mechanical energy of the ultrasound waves can also produce gentle fluid movement around the cells, further facilitating the healing process and reducing inflammation.

In accordance with an exemplary embodiment of the claimed invention, as shown in FIGS. 5-9, the anatomical manipulation device 1000 comprises various types of therapeutic stimulators, such as electrical Doppler sensor 1300, muscle stimulators 1500, thermal pad 1600, piezoelectric transducers 1700, micro-vibrators 3000 and electromyography (EMG) electrode 3100, to deliver specialized manipulation motions tailored to target the base of the skull (the occiput) and the top cervical vertebra (C1) to relieve pressure on the vertebral and jugular veins, enhancing blood and cerebrospinal fluid flow. This area is critical for both neurological and vascular function due to its proximity to the brainstem, vertebral arteries, jugular veins, and cerebrospinal fluid pathways. This includes compressive forces applied by the vibrating elements and shearing actions produced by the actuator 1100.

The timing, duration, intensity, and technique selection of these dynamic actuations are programmatically controlled by the anatomical manipulation device's controller 2000 comprising embedded electronics and software.

Preset programs apply manipulation routines following evidence-based best practices matched to a given medical condition and/or symptoms, based on the recommended parameters. Adaptive plans also adjust the stimulation protocols and/or algorithms based on quantitative user feedback, helping personalize and improve comfort and effectiveness.

Modular Hardware Attachments

Figure 10:
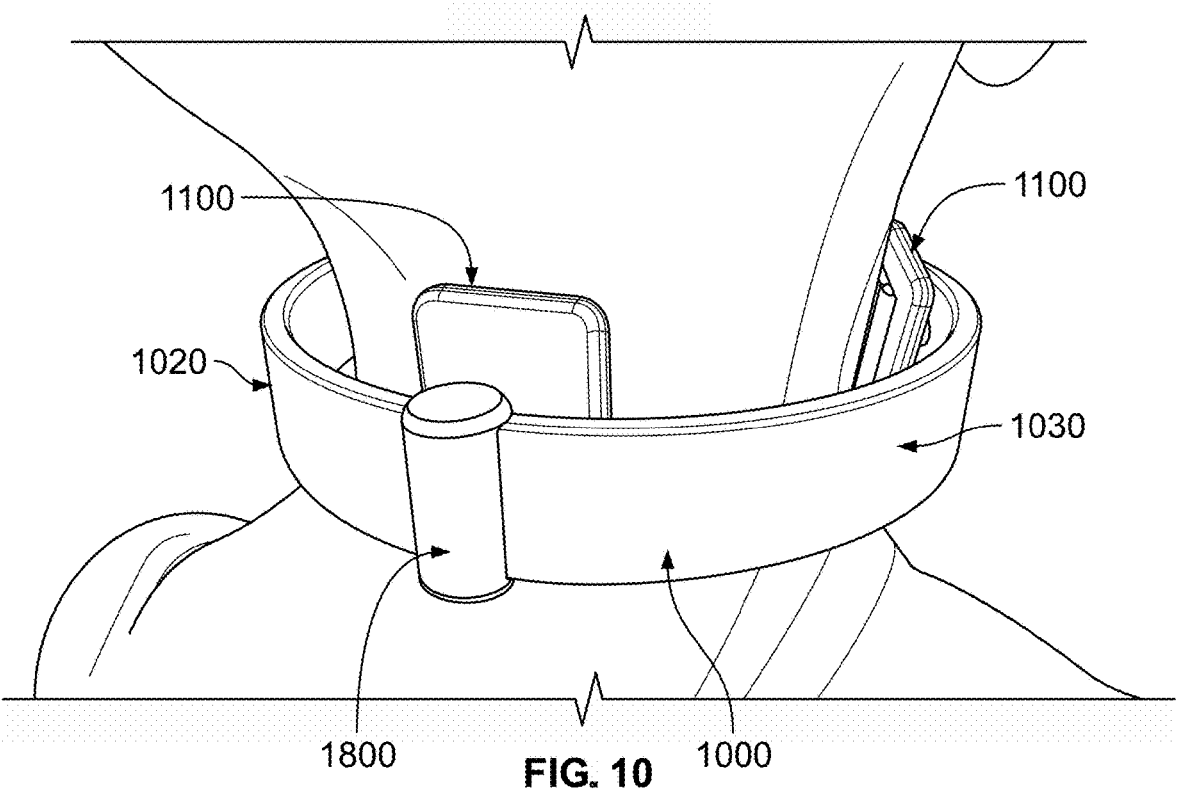
FIG. 10 a perspective view of the anatomical manipulation device worn by the user in accordance with an exemplary embodiment of the claimed invention.

In accordance with an exemplary embodiment of the claimed invention, as shown in FIG. 10 the actuator connectors 1200 of the anatomical manipulation device 1000 provides mounting interfaces and data transfer to facilitate interconnection of a plurality of modular attachments for augmenting the core manipulation capabilities:

Ultrasound imaging probes equipped with Doppler flow metering to perform volumetric analysis of vascular structures during therapy. This allows quantifying hemodynamic impacts on cranial blood flow resulting from the cervical manipulations in real time.

Electrical muscle stimulators 1500 with adjustable electrodes provide targeted stimulation of various motor points to prompt muscle activations before, during or after manipulation routines—helping strengthen muscular tone.

Thermal therapy attachments circulate cooled or heated fluids through conformal pads to effectively transfer heat and improve circulation.

The integration of these optional hardware modules expands the system's capabilities for advanced therapy characterization, supplemental muscle stimulation, and thermal regulation—further enhancing therapeutic scope.

Software Analytics Modules

Supplemental analytics software plug-ins help further customize therapy by analyzing inputs from sensors like:

Feedback devices, preferably wearable feedback devices, quantifying EEG, heart rate, skin conductance, which reflect stress levels allowing massages to be modulated for greater relaxation.

Proprietary sensor fusion algorithms that combine various modalities to estimate overall real-time efficacy scores of the therapy session, projecting future results to maximize outcomes.

Adjustability and Ergonomics

The intensity, duration, frequency, and location of diverse massage and manipulation stimulations are adjustable by user via communication interface 2030, which can be wired or wireless interface. The housing of the anatomical manipulation device 1000 incorporates an ergonomic form-factor with padded contact surfaces designed for stable and comfortable head/neck interface.

In accordance with an exemplary embodiment of the claimed invention, as shown in FIGS. 1-4, the anatomical manipulation device 1000 is a carotid massager 1000 to stimulate cerebral blood flow and cerebrospinal fluid. The carotid massager 1000 comprises an anatomical interface 1010 to encircle the neck of a user, as exemplary shown in FIG. 10.

In accordance with an exemplary embodiment of the claimed invention, as shown in FIG. 10, the anatomical interface 1010 comprises a first section 1020 and a second section 1030 connected by an interface connector 1800. The first section 1020 and the second section 1030 are rotatably and removably connected to each other by a neck connector 1800. Each actuator 1100 is rotatably and removably connected to the anatomical interface 1010 by an actuator connector 1200. As exemplary shown in FIGS. 1-4, the three actuator connectors 1200 are configured to adjust the rotational movements of the three connected actuators 1100. In accordance with an exemplary embodiment of the claimed invention, the interface connector 1800 is configured to adjust the circumference of the carotid massager 1000 to accommodate varying neck sizes of the users by moving the non-connected ends of the two sections 1020, 1030 of the anatomical interface 1010 closer to or further from each other.

The controller 2000 coordinates therapeutic responses by activating a set of said plurality of actuators in a programmed pattern, modifying a collective therapeutic output based on the coordinated therapeutic responses, and adjusting therapeutic parameters based on the measured responses. The anatomical manipulation device 1000 further comprises a communication interface 2030 to connect to an external device 5000 to provide a real-time 2D or 3D visualization of a therapeutic activity, a spatial tracking to monitor the collective therapeutic output and a gesture control to enable a user to adjust the therapeutic parameters.

In accordance with an exemplary embodiment of the claimed invention, the coordinated therapeutic responses comprise a sequential activation of an actuator positioned on the user's posterior to an actuator position on the user's anterior. That is, the three actuators 1100 exemplary shown in FIGS. 1, 2, 4 and 10 are activated one at a time in a sequence.

In accordance with an exemplary embodiment of the claimed invention, the coordinated therapeutic responses comprise a sequential activation of an actuator comprising a different type of stimulator. That is, each of the three actuators 1100 exemplary shown in FIGS. 1, 2, 4 and 10 comprise a different type of therapeutic stimulators and are activated one at a time in a sequence.

In accordance with an exemplary embodiment of the claimed invention, the coordinated therapeutic responses comprise a synchronized intensity modulation of the actuators.

In accordance with an exemplary embodiment of the claimed invention, the coordinated therapeutic responses comprise a wave activation sequence of the actuators. Each step in the sequence can have different pitch, duration, fine tuning, level, and crossfade amount.

In accordance with an exemplary embodiment of the claimed invention, the controller 2000 stores effective actuator combination patterns, learns optimal activation sequences, adapts actuator combination patterns based on the coordinated therapeutic responses, and modifies a timing between activation of the actuators.

In accordance with an exemplary embodiment of the claimed invention, the controller 2000 is configured to trigger, based on the measured physiological response, predefined actuator combination responses and/or adaptive pattern modifications and/or intensity adjustments across multiple actuators and/or modification to activation timing and sequence of the actuators.

In accordance with an exemplary embodiment of the claimed invention, the programmed patterns comprise drainage enhancement sequences, circulation improvement combinations, pressure relief patterns, or tissue mobilization sequences.

Figure 11:
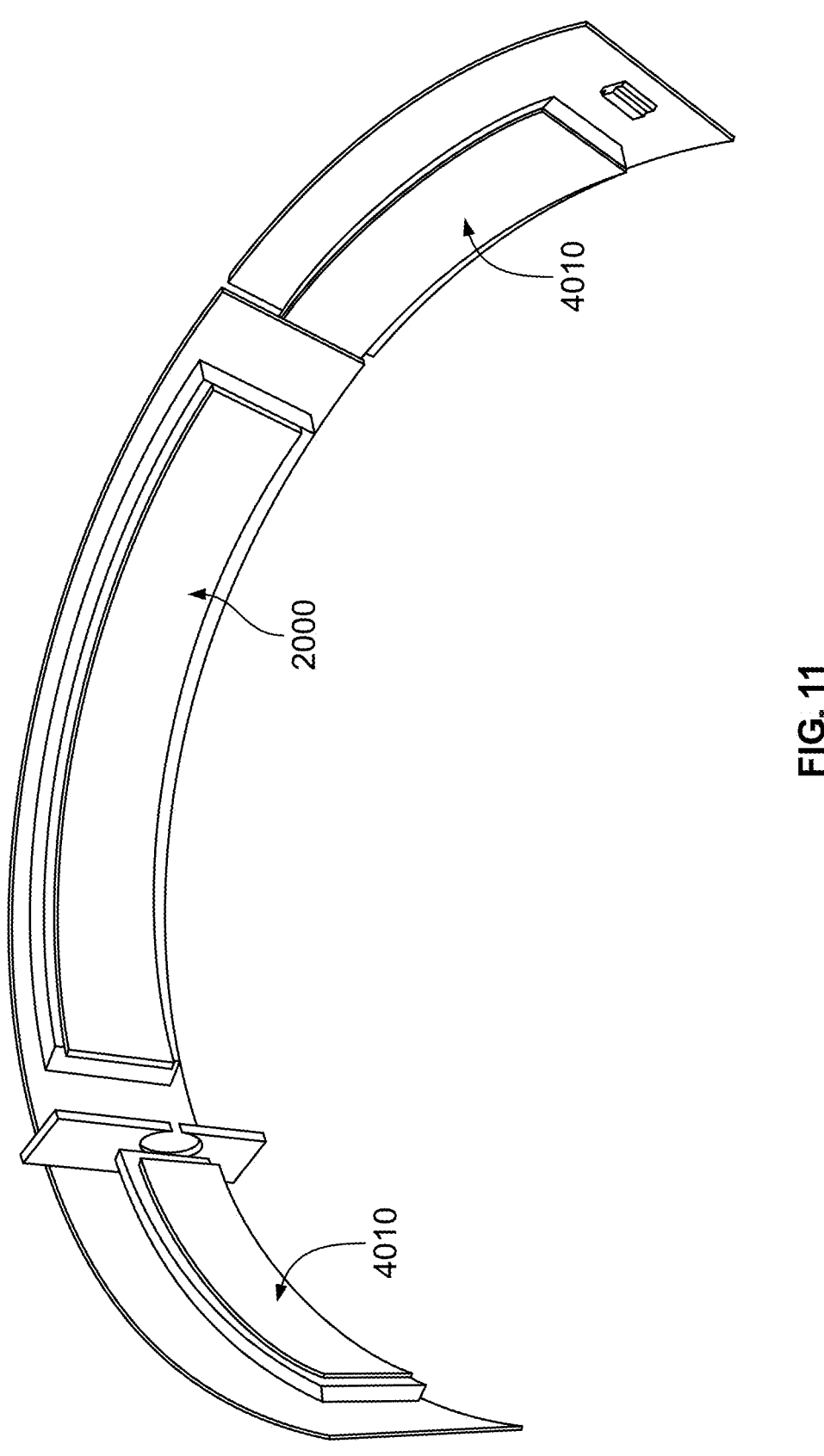
FIG. 11 is a perspective view of the anatomical manipulation device with rechargeable battery housing in accordance with an exemplary embodiment of the claimed invention.

In accordance with an exemplary embodiment of the claimed invention, the anatomical manipulation device 1000 further comprises a power supply 4000. The controller 2000 manages power of the power supply 4000 by adjusting monitoring frequency based on power availability and/or prioritizing therapeutic functions over data collection and/or optimizing sampling rates for battery life and/or enabling enhanced monitoring when an external power source is utilized. Preferably, as exemplarily shown in FIG. 11, the power supply 4000 is a rechargeable battery housed within the anatomical interface 1010 accessible through the battery cover 4010.

In accordance with an exemplary embodiment of the claimed invention, the HIFU probes 1400 are configured to perform at least one of the following: target deep cervical lymph nodes, monitor blood flow at configurable intervals and store measured flow response data.

In accordance with an exemplary embodiment of the claimed invention, the micro-vibrators 3000 target the Atlanto-occipital joint, automatically adjust based on the measured responses, coordinate timing with HIFU therapy, and maintain vibration within safe frequency ranges.

There are four different frequency ranges: 5-50 Hz for whole-body vibration, 20-80 Hz for localized vibration therapy, 5-20 Hz for low-frequency vibration for neurological or therapeutical applications, and 50-120 Hz for high-frequency vibration for tissue healing.

In accordance with an exemplary embodiment of the claimed invention, the safe frequency range for therapeutic is 0.75-3 MHz and for HIFU therapy is 3.8-7.5 MHz. In low-frequency stimulation, the pulse frequency of the micro-vibrators 3000 is in the range of 1-10 Hertz (Hz) for relaxation and recovery. For muscle strength and endurance training, the pulse frequency of the micro-vibrators 3000 is in the range of 20-50 Hz. For high-intensity stimulation targeting muscle growth or rehabilitation, the pulse frequency of the micro-vibrators 3000 is in the range of 50-100 Hz.

In accordance with an exemplary embodiment, the ultrasound probes operate in the range of 2 MHz to 15 MHz for diagnostic applications. The ultrasound probes operate in the range of 0.75 MHz to 3 MHz for therapeutic applications, preferably at 1 MHz and 3 MHz. The focused ultrasound probes and the HIFU probes 1400 operate at various frequencies ranging from 3.8 MHz to 7.5 MHz.

In accordance with an exemplary embodiment of the claimed invention, the electrical muscle stimulators 1500 provide targeted muscle activation, adjust intensity based on electromyographic (EMG) feedback, synchronize with other therapeutic stimulators and prevent muscle fatigue through adaptive timing.

In accordance with an exemplary embodiment of the claimed invention, the electrical muscle stimulators (EMS) 1500 adjusts the timing of electrical impulses to align with the natural muscle contraction and relaxation cycles. This ensures that the stimulation is synchronized with the physiological needs of the muscle for optimal comfort, efficiency, and effectiveness.

As muscles fatigue, their responsiveness to electrical stimulation can change. In accordance with an exemplary embodiment of the claimed invention, the adaptive timing of the EMS 1500 dynamically adjusts the pulse timing or waveform to maintain effectiveness while reducing discomfort, thereby providing dynamic adjustment to account for muscle fatigue.

In accordance with an exemplary embodiment of the claimed invention, the EMS 1500 synchronizes with muscle contractions. That is, the EMS 1500 monitors the muscle's natural contraction rhythm and adjusts its impulses to complement or enhance it, providing more natural movement and reducing strain.

In accordance with an exemplary embodiment of the claimed invention, the EMS 1500 provides personalized pulse delivery. The EMS 1500 uses sensors to detect muscle response in real-time, adjusting parameters such as pulse width, frequency, and duration for the individual user.

In accordance with an exemplary embodiment of the claimed invention, the timing parameters of the EMS 1500 with adaptive features comprise pulse frequency, pulse width, ramp time and on/off cycle timing. In low-frequency stimulation, the pulse frequency of the EMS 1500 is in the range of 1-10 Hertz (Hz) for relaxation and recovery. For muscle strength and endurance training, the pulse frequency of the EMS 1500 is in the range of 20-50 Hz. For high-intensity stimulation targeting muscle growth or rehabilitation, the pulse frequency of the EMS 1500 is in the range of 50-100 Hz.

The range of pulse width of the EMS 1500 is in the range of 50-400 μs, adjusted based on muscle size and stimulation intensity. It is appreciated that gradual increase or decrease in intensity of the EMS 1500 over 1-5 seconds of ramp time (rise/fall) reduces discomfort during the start and end of stimulation. Additionally, the EMS 1500 provides on/off cycle timing with alternating stimulation and rest periods. The on/off cycle timing ratio of 10 seconds on and 20-30 seconds off allows muscle recovery.

In accordance with an exemplary embodiment of the claimed invention, the adaptive timing of the EMS 1500 advantageously enables the anatomical manipulation device 1000 to be used for many applications. The anatomical manipulation device 1000 can be used for rehabilitation therapy by tailoring the stimulation to aid recovery from injury without overstimulating fragile or healing tissues; for athletic performance training to enhance muscle strength, endurance, and recovery by aligning with the muscle's natural capabilities during intense sessions; for chronic pain management to provide targeted relief by ensuring continuous but comfortable stimulation of affected areas; and for post-surgical recovery to optimizes timing to prevent atrophy and support healing in immobilized or weakened muscles.

In accordance with an exemplary embodiment of the claimed invention, the adaptive timing of the EMS 1500 provides the following benefits: improved comfort to reduce the risk of overstimulation or pain during use, enhanced efficiency to maximize muscle recruitment by aligning impulses with physiological needs, minimize fatigue by adjusting to muscle responsiveness, preventing overuse or exhaustion, and personalization to ensures stimulation is tailored to the individual's muscle type, condition, and goals.

In accordance with an exemplary embodiment of the claimed invention, the aforesaid controller analyzes therapy effectiveness through at least one of the following: comparison of pre-measurements and post-measurements, trend analysis across sessions, identification of optimal therapeutic parameters and patient-specific response patterns.

In accordance with an exemplary embodiment of the claimed invention, at least one of the aforesaid actuators comprises a Doppler sensor to monitor and diagnose ultrasound blood flow quantification and electroencephalogram (EEG) brain activity In accordance with an exemplary embodiment of the claimed invention, the aforesaid Doppler sensor comprises a HIFU probe configured to generate ultrasound waves and electrical muscle stimulators on each side of the ultrasound probe, the electrical muscle stimulators are configured to provide percussive pulsations.

In accordance with an exemplary embodiment of the claimed invention, each aforesaid ultrasound probe comprises a thermal pad to stimulate a flow of blood and cerebrospinal fluid along a lymphatic vessel and a lymph node to prevent accumulation of beta amyloid and tau proteins in user's brain and body. A piezoelectric transducer is enclosed within the thermal pad.

In accordance with an exemplary embodiment of the claimed invention, the aforesaid piezoelectric transducer is configured to reduce noise coupling, enhance resolution and enable gel-free acoustic coupling.

In accordance with an exemplary embodiment of the claimed invention, the aforesaid piezoelectric transducer is configured to transmit bounced-back biofeedback waves to the controller; and wherein the controller analyzes biofeedback data.

In accordance with an exemplary embodiment of the claimed invention, the aforesaid controller further comprises preset manipulation protocols optimized for a predetermined medical condition; and adaptive lesson plans to customize therapy based on user feedback.

In accordance with an exemplary embodiment of the claimed invention, the aforesaid device further comprises electromyography electrodes on skin surface and a biofeedback device quantifying EEG and heart rate. The aforesaid controller integrates signals from at least one of electromyography electrodes and the biofeedback device.

In accordance with an exemplary embodiment of the claimed invention, the aforesaid feedback device is at least one of a wearable device, a smartphone, a tablet, a laptop, a personal computer, a virtual reality/augmented reality (VR/AR) headset.

In accordance with an exemplary embodiment of the claimed invention, the aforesaid micro-vibrators are positioned to target anatomical areas affecting cranial, cervical, and upper back fluid drainage and circulation.

In accordance with an exemplary embodiment of the claimed invention, the aforesaid micro-vibrators are configured to improve venous drainage from a user's head and neck and configured to reduce a cerebrospinal fluid pressure by improving venous return from the user's brain.

In accordance with an exemplary embodiment of the claimed invention, a soft tissue mobilization of micro-vibrators relaxes upper trapezius, sternocleidomastoid (SCM), and scalene muscles, thereby reducing a venous obstruction in the user's neck.

In accordance with an exemplary embodiment of the claimed invention, the anatomical manipulation device comprises 1000 a plurality of actuators 1100 configured to apply therapeutic manipulation forces to targeted regions of a user's head, neck or upper back based on baseline technique protocols. Preferably, the anatomical manipulation device 1000 comprises different types of therapeutic stimulators and embedded sensors to monitor device/user biomechanics for internal feedback-based control of manipulations. Additionally, the anatomical manipulation device 1000 comprises communication interfaces 2030, e.g., wired or wireless interface to support wireless connectivity to enable data transmission protocols to connect with supplemental feedback devices 5000 including wearable devices, smartphones, tablets, laptops, personal computers (PCs), and virtual reality/augmented reality (VR/AR) headsets.

In accordance with an exemplary embodiment of the claimed invention, the anatomical manipulation device 1000 can additionally comprise electroencephalogram (EEG) monitors, fitness wearables, and ultrasound/Doppler probes.

In accordance with an exemplary embodiment of the claimed invention, the controller 2000 of the aforesaid anatomical manipulation device 1000 is configured to execute software protocols guiding actuation timing, intensity, and technique selection while dynamically tuning the manipulation parameters in real-time based on the sensor data and supplemental device inputs to optimize therapy delivery.

In accordance with an exemplary embodiment of the claimed invention, the plurality of actuators 1100 comprise Doppler probes 1300 and/or vibrating elements, such as piezoelectric transducers 1700 and/or micro-vibrators 3000 providing percussive pulsations, and/or elements generating shearing motions.

In accordance with an exemplary embodiment of the claimed invention, the anatomical manipulation device 1000 further comprises interchangeable modular attachments expanding manipulation capabilities, such as a feedback device to quantify EEG and heart rate, micro-vibrators 3000 to reduce venous obstruction and improve fluid drainage and circulation, EMG electrodes 3100 to measure muscle activity, Doppler probes 1300 for blood flow analysis; electrical muscle stimulators 1500, and the thermal pads 1600 for stimulating a flow of blood and cerebrospinal fluid along a lymphatic vessel and a lymph node.

In accordance with an exemplary embodiment of the claimed invention, the controller 2000 further comprises preset manipulation protocols optimized for a medical condition grounded in literature; and adaptive lesson plans customizing therapy based on user feedback.

In accordance with an exemplary embodiment of the claimed invention, the controller 2000 is configured to integrate signals from the EMG electrodes 3100 on skin surface and/or feedback devices quantifying EEG and heart rate.

In accordance with an exemplary embodiment of the claimed invention, the anatomical manipulation device 1000 further comprises thermal pads 1600 using ultrasound waves to stimulate a flow of blood and cerebrospinal fluid along a lymphatic vessel and a lymph node to prevent accumulation of beta-amyloid and tau proteins in user's brain and body. Beta-amyloid and hyperphosphorylated tau are hallmark lesions of Alzheimer disease. Alzheimer's-related brain changes result from a complex interplay among abnormal tau and beta-amyloid proteins.

The claimed invention, having been described, will make apparent to those skilled in the art that the same may be varied in many ways without departing from the spirit and scope of the invention. Any and all such modifications are intended to be included within the scope of the following claims.

The invention claimed is:

1. An anatomical manipulation device comprising:
   a plurality of actuators configured to be positioned around an anatomical interface of a neck;
   at least one feedback sensor to measure one or more physiological responses related to a cerebrospinal fluid flow;

an interactive communication interface to receive input from a user;

a controller to coordinate operation of said plurality of actuators based on measurements received from said at least one feedback sensor and said input from the interactive communication interface to enhance a cerebrospinal fluid circulation and a cerebrospinal fluid drainage a thermal pad configured to enhance the cerebrospinal fluid flow by stimulating blood and cerebrospinal fluid along a lymphatic vessel and a lymph node to prevent accumulation of beta amyloid and tau proteins in user's brain and body; and a piezoelectric transducer, enclosed within the thermal pad, to reduce noise coupling, enhance resolution and enable gel-free acoustic coupling to enhance the cerebrospinal fluid flow; and wherein the piezoelectric transducer transmits bounced-back feedback waves to the controller for monitoring cerebrospinal fluid flow patterns.

2. The device of claim 1, wherein each of said plurality of actuators comprises one or more of:

a first high-intensity focused ultrasound (HIFU) probe configured to enhance the cerebrospinal fluid flow by targeting cervical lymph nodes and a second HIFU probe configured to monitor the cerebrospinal fluid flow by monitoring blood flow at configurable intervals set by the controller;

an electrical muscle stimulator configured to enhance the cerebrospinal fluid flow by providing a targeted muscle activation, the operation of the electrical muscle stimulator being coordinated by the controller to adjust intensity based on the measurements from said at least one feedback sensor, synchronize with other therapeutic stimulators and prevent muscle fatigue through adaptive timing;

a low-frequency pulse generator operating in a pulse frequency range of 1-50 Hz configured to enhance the cerebrospinal fluid flow; and a micro-vibrator configured to be positioned to target anatomical areas affecting cerebrospinal fluid pathways, cranial, cervical, and upper back fluid drainage and circulation to enhance the cerebrospinal fluid flow; and wherein said plurality of actuators is configured to be arranged in a pattern around the anatomical interface to enable a sequential activation from posterior to anterior positions to enhance the cerebrospinal fluid flow.

3. The device of claim 2, wherein the controller coordinates the operation of said plurality of actuators by one of the following: sequentially activating said plurality of actuators one at a time, in a synchronized intensity modulation, or in a wave activation sequence.

4. The device of claim 1, wherein the controller is configured to coordinate activation sequences of said plurality of actuators to enhance the cerebrospinal fluid flow, to modify therapeutic parameters based on the measurements from said at least one feedback sensor, to store effective activation patterns for future use, and to modify a timing between activation of said plurality of actuators to optimize the cerebrospinal fluid flow.

5. The device of claim 4, wherein the controller is configured to analyze deviations from baseline measurements related to the cerebrospinal fluid flow and to coordinate activation of a set of said plurality of actuators in one of the stored effective patterns to enhance the cerebrospinal fluid flow.

6. The device of claim 1, wherein the interactive communication interface provides a real-time visualization of a therapeutic activity, a spatial tracking to monitor a therapeutic output and a gesture control to enable a user to adjust therapeutic parameters.

7. The device of claim 1, wherein said at least one feedback sensor further comprises one of the following:

an electromyographic (EMG) electrode to monitor muscle tension affecting the cerebrospinal fluid flow, an electroencephalography (EEG) sensor to monitor brain activity changes related to the cerebrospinal fluid circulation, a heart rate sensor to track cardiovascular responses affecting cerebrospinal fluid dynamics; and a Doppler sensor to monitor and diagnose ultrasound blood flow quantification in a head and neck region affecting the cerebrospinal fluid circulation.

8. The device of claim 1, wherein said plurality of actuators comprises:

a first high-intensity focused ultrasound (HIFU) probe configured to enhance the cerebrospinal fluid flow by targeting cervical lymph nodes and a second HIFU probe configured to monitor the cerebrospinal fluid flow by monitoring blood flow at configurable intervals set by the controller;

a micro-vibrator configured to be positioned to target anatomical areas affecting cerebrospinal fluid pathways, cranial, cervical, and upper back fluid drainage and circulation to enhance the cerebrospinal fluid flow; and wherein the controller is configured to operate the micro-vibrator to target the Atlanto-occipital joint, to automatically adjust based on the measurements, to coordinate timing with HIFU therapy, and for a therapeutic purpose, to maintain vibration within a frequency range of 0.75-7.5 MHz.

9. The device of claim 8, wherein the controller is configured to operate the micro-vibrator to improve venous drainage from a user's head and neck and configured to reduce a cerebrospinal fluid pressure by improving venous return from the user's brain.

10. The device of claim 9, wherein the controller is configured to operate the micro-vibrator to enhance the cerebrospinal fluid flow by providing a soft tissue mobilization to relaxes the user's upper trapezius, sternocleidomastoid and scalene muscles in a head and neck region, thereby reducing a venous obstruction in the user's neck which facilitates the cerebrospinal fluid drainage.

11. The device of claim 1, wherein, based on the measurements from said at least one feedback sensor, the controller is configured to trigger at least one of the following: predefined actuator combination responses to enhance the cerebrospinal fluid flow, adaptive pattern modifications, intensity adjustments across multiple actuators and modification to activation timing and sequence of said plurality of actuators.

12. The device of claim 1, wherein said plurality of actuators are activated in one of the following programmed patterns to enhance the cerebrospinal fluid flow: a drainage enhancement sequence, a circulation improvement combination, a pressure relief pattern, and a tissue mobilization sequence.

13. The device of claim 1, wherein the controller analyzes therapy effectiveness for enhancing the cerebrospinal fluid flow through at least one of the following: comparison of pre-measurements and post-measurements of cerebrospinal fluid flow indicators, trend analysis across sessions, identification of optimal therapeutic parameters for a cerebrospinal fluid enhancement and patient-specific response patterns.

14. The device of claim 1, wherein the controller further comprises preset manipulation protocols optimized for a predetermined medical condition affecting the cerebrospinal fluid circulation to enhance the cerebrospinal fluid flow; and adaptive lesson plans to customize therapy based on user feedback.

15. The device of claim 1, further comprising at least one of the following feedback devices configured to monitor cerebrospinal fluid flow indicators: a wearable device, a smartphone, a tablet, a laptop, a personal computer, a virtual reality/augmented reality (VR/AR) headset.

16. The device of claim 1, further comprising a power supply; and wherein the controller manages power of the power supply by at least one of the following: adjusting monitoring frequency based on power availability; prioritizing therapeutic functions over data collection; optimizing sampling rates for battery life; and enabling enhanced monitoring when an external power source is utilized.

17. The device of claim 16, wherein the power supply is at least one of a rechargeable battery and an external power source.

* * * * *